United States Patent
Itsuji

(10) Patent No.: US 7,608,826 B2
(45) Date of Patent: Oct. 27, 2009

(54) SPECIMEN TESTING ELEMENT, SPECIMEN INFORMATION OBTAINING METHOD AND SPECIMEN TESTING APPARATUS

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 465 days.

(21) Appl. No.: 11/468,063

(22) Filed: Aug. 29, 2006

(65) Prior Publication Data
US 2007/0108382 A1    May 17, 2007

(30) Foreign Application Priority Data
Sep. 5, 2005    (JP) ............................. 2005-256545

(51) Int. Cl.
*G01J 5/02*    (2006.01)
(52) U.S. Cl. ................................. 250/341.1
(58) Field of Classification Search .... 250/341.1–341.8
See application file for complete search history.

(56) References Cited

U.S. PATENT DOCUMENTS

| | | | | |
|---|---|---|---|---|
| 5,623,145 | A | 4/1997 | Nuss | 250/330 |
| 5,710,430 | A | 1/1998 | Nuss | 250/358.1 |
| 2006/0273255 | A1* | 12/2006 | Volkov et al. | 250/336.1 |
| 2007/0004046 | A1* | 1/2007 | Abbott | 436/104 |

FOREIGN PATENT DOCUMENTS

| | | |
|---|---|---|
| JP | 8-320254 | 12/1996 |
| JP | 2004-120260 | 4/2004 |

OTHER PUBLICATIONS

Nagai et al., "Integrated THz biomolecular sensors for DNA," 2002, IEEE, Terahertz electroncs proceedings, pp. 70-73.*
Bolivar et al., "THz sensing of genes," 2000, Optical Society of America, Ultrafast technology for medical and biomedical optics, pp. CMB5.*

(Continued)

*Primary Examiner*—David P Porta
*Assistant Examiner*—Kiho Kim
(74) *Attorney, Agent, or Firm*—Fitzpatrick, Cella, Harper & Scinto

(57) ABSTRACT

A specimen testing element, a specimen information obtaining method and a specimen testing apparatus is used to obtain information on a specimen by utilizing a specific phenomenon attributable to wavelength selectivity, resonance characteristics and so on. The specimen testing element obtains information on a specimen by utilizing a change in the propagation state of an electromagnetic wave propagating through a transmission path due to the existence of a specimen. A plurality of holding portions capable of holding a specimen are arranged substantially in a predetermined mode of regularity in part of a region in the transmission path where the propagating electromagnetic wave exists to form a specimen holding body. The specimen is filled in the plurality of holding portions by a specimen filling means and the electromagnetic wave propagating through the transmission path is detected by an electromagnetic wave detecting means.

12 Claims, 7 Drawing Sheets

OTHER PUBLICATIONS

Fischer et al., "Chemical recognition in terahertz time-domain spectroscopy and imaging," 2005, semiconductor science and technology, vol. 20. pp. S246-S253.*

Bocquet et al., "Design of silicon-PPTMDS bio-MEMS by cold RPECVD," Proceedings of SPIE, vol. 5345, pp. 118-129.*

Baras et al., "Design considerations for on-chip THz analysis of biomolecules," 2002, IEEE, Terahertz electronics Proceedings, pp. 77-80.*

Ferguson et al., "Terahertz imaging of biological tissue using a chirped probe pulse," 2001, Proceedings of SPIE, vol. 4591, pp. 172-184.*

Koch, "THz-imaging: Fundamentals and Biological Applications," Proceedings of SPIE, vol. 3828, pp. 202-208.*

M. Nagel, et al., "Integrated THz Technology for Label-Free Genetic Diagnostics", Applied Physics Letters, vol. 80, No. 1, pp. 154-156 (Jan. 7, 2002).

* cited by examiner

SPECIMEN TESTING ELEMENT, SPECIMEN INFORMATION OBTAINING METHOD AND SPECIMEN TESTING APPARATUS

BACKGROUND OF THE INVENTION

1. Field of the Invention

The present invention relates to a specimen testing element, a specimen information obtaining method and a specimen testing apparatus for obtaining information on a specimen typically by analyzing the physical properties of the specimen by means of an electromagnetic wave.

2. Description of the Related Art

Non-destructive testing techniques utilizing a high frequency electromagnetic wave with an appropriate band in the frequency range extending from millimeter waves to tera-hertz waves (30 GHz to 30 THz) (to be also referred to as a tera-hertz wave hereinafter) have been developed in recent years. It has been known that absorbable rays capable of being absorbed by various substances including bio molecules are found in the frequency range of tera-hertz wave. Harmless imaging techniques that utilize electromagnetic waves of the above cited frequency zone for see-through examination instruments instead of X-rays are available. Spectral techniques for determining the absorption spectrum and the complex dielectric constant in the inside of a substance to look into the coupled condition of molecules are also available. Techniques for analyzing bio molecules and those for evaluating the carrier density and mobility that utilize electromagnetic waves of the above cited frequency zone are also expected.

An object testing apparatus that utilizes a tera-hertz wave and has a configuration as illustrated in FIG. 10 of the accompanying drawings is known (Japanese Patent Application Laid-Open No. H08-320254). The testing apparatus disclosed in the above-cited patent document is designed to irradiate a tera-hertz wave that propagates in space onto an object 10 and observe the component material or materials of the object by means of the change in the propagation state of the wave transmitted through the object. Thus, a penetrative image of the inside of the object can be obtained by two-dimensionally scanning the object.

With the above-described technique, a tera-hertz wave is made to propagate by way of space. However, it is popularly known that a tera-hertz wave propagates through many transmission paths that are being used to propagate high frequency electromagnetic wave signals. Therefore, it is possible to control the propagation state of a tera-hertz wave like any other high frequency electromagnetic waves. For the purpose of controlling the propagation state of a tera-hertz wave, there has been proposed a method of arranging a first electrode 11 and a second electrode 12 on a substrate 13 to form a transmission path and periodically arranging dielectric bodies 14 having different dielectric constants on a part of the a dielectric substrate 13 as shown in FIG. 11 of the accompanying drawings (Japanese Patent Application Laid-Open No. 2004-120260). A photonic band gap is formed as the dielectric constants are changed with lattice gap d and period a so that it is possible to add a sort of resonance structure to the transmission path and filter a part of the signal component of the high frequency electromagnetic wave propagating through the transmission path.

A device illustrated in FIG. 12 of the accompanying drawings is designed to couple a tera-hertz wave onto a transmission path having an optical switch region 21 and a filter region 22 so as to apply it to a DNA sensor (Appl. Phys. Lett., Vol. 80, No. 1, p154-p156, 2002). The coupling state of the spiral structure of DNA is detected from the change in the propagation state of the tera-hertz wave propagating through the transmission path.

Generally, a tera-hertz wave is strongly absorbed by water. Japanese Patent Application Laid-Open No. H08-320254 discloses an arrangement for detecting a tera-hertz wave transmitted through a specimen for the purpose of detecting the physical properties of the specimen. However, as a tera-hertz wave is propagated through the atmosphere, it is attenuated to a large extent by the moisture in the atmosphere. To alleviate the influence of the atmosphere, a technique of adjusting the atmosphere is required for a region surrounding the propagation path of the tera-hertz wave. Then, the entire arrangement is forced to involve large dimensions due to the means for adjusting the atmosphere. Additionally, when the specimen itself shows a strong absorption characteristic relative to tera-hertz waves, the output of the transmitted tera-hertz wave is weakened due to the absorption by the specimen. Such a problem may be avoided when the specimen is made to show a profile of a thin film to effectively reduce the extent to which the tera-hertz wave is absorbed by the specimen. However, such an arrangement will degrade the detection sensitivity because the part of the specimen that interacts with the tera-hertz wave (the quantity of the specimen in the tera-hertz wave transmitting direction) is also reduced. Additionally, an additional step of processing the specimen will be required.

When a transmission path as disclosed in Japanese Patent Application Laid-Open No. 2004-120260 is used, the high frequency electromagnetic wave that propagates through the transmission path concentrates in the dielectric substrate that provides the transmission path, although the extent of concentration may vary depending on the profile of the transmission path. Therefore, when such an arrangement is applied to transmission of a tera-hertz wave, it may not be possible to suppress the attenuation of the signal due to the atmosphere because the tera-hertz wave concentrates in the substrate. However, no technique has been disclosed to date for controlling the propagation state of the tera-hertz wave in a transmission path by using a band gap formed according to Japanese Patent Application Laid-Open No. 2004-12060 and applying the technique to testing a specimen.

The DNA sensor disclosed in Appl. Phys. Lett., Vol. 80, No. 1, p154-p156, 2002 employs a micro-strip line 23 as transmission path. Then, the DNA, or the specimen 24, is dropped on a conductor of the micro-strip line. The tera-hertz wave that propagates through the transmission path concentrates in the dielectric substrate 25 that is sandwiched between the two conductors of the micro-strip line. Therefore, only the tiny electromagnetic wave leaking out to the vicinity of the conductors is used as a tera-hertz wave for sensing the specimen. In short, the efficiency of utilization of a tera-hertz wave is low for the detecting operation. Thus, there is a demand for specimen testing elements showing a high efficiency of utilization of a tera-hertz wave.

SUMMARY OF THE INVENTION

According to the present invention, there is provided a specimen testing element for obtaining information on a specimen by utilizing a change in the propagation state of an electromagnetic wave propagating through a transmission path due to the existence of a specimen, a plurality of holding portions capable of holding a specimen being arranged substantially in a predetermined mode of regularity in part of a region in the transmission path where the propagating electromagnetic wave exists. Typically, the transmission path has one or more than one conductors and a dielectric material and the holding portions are formed in the dielectric material, while the conductors are formed so as to adhere to the surface of the dielectric material at least in order to confine the electromagnetic field to the sites where the holding portions exist. The holding portions are formed as so many voids with a modulated refractive index in a predetermined space of the dielectric material. For the purpose of the present invention, when the transmission path has one or more than one conductors and a dielectric material, the frequency range of electromagnetic wave to be handled is typically not higher than several THz where tera-hertz waves are found. However, electromagnetic waves of frequencies out of the above frequency rage may be handled depending on the frequency characteristics of the dielectric material and the configuration of the transmission path.

In view of the above identified circumstances, according to the present invention, there is provided a specimen information obtaining method of obtaining information on a specimen by utilizing a change in the propagation state of an electromagnetic wave propagating through a transmission path, a plurality of holding portions capable of holding a specimen being arranged substantially in a predetermined mode of regularity, the electromagnetic wave being propagated so as to cover at least a region of the transmission path where a plurality of holding portions are found and being detected to obtain information on the specimen.

In view of the above identified circumstances, according to the present invention, there is provided a specimen testing apparatus comprising a specimen testing element as defined above, a specimen filling means for filling a specimen in the plurality of holding portions, an electromagnetic wave generating means for propagating an electromagnetic wave through the transmission path and an electromagnetic wave detecting means for detecting an electromagnetic wave propagating through the transmission path. A specimen testing apparatus may further comprise a database for storing information on specimens and a comparing section for collating the information of the database and electromagnetic wave information detected by the electromagnetic wave detecting means to obtain information on the specimen. A specimen testing apparatus according to the present invention may further comprise a presenting section for presenting the obtained information.

Thus, with a specimen testing element, a specimen information obtaining method and a specimen testing apparatus comprising a specimen testing element according to the present invention, a plurality of holding portions capable of holding a specimen is arranged substantially in a predetermined mode of regularity in the region of a transmission path where an electromagnetic wave propagating through the transmission path to form a specimen testing element. A specimen is held by the holding portions and information on the specimen including physical properties of the specimen is detected by utilizing that the propagation state of the electromagnetic wave coupled to the specimen detecting element changes. Therefore, it is possible to obtain information on a specimen by utilizing a specific phenomenon arising from the wavelength selectivity and the resonance characteristics attributable to the substantially regular arrangement of a plurality of holding portions holding the specimen.

Further features of the present invention will become apparent from the following description of exemplary embodiments (with reference to the attached drawings).

DESCRIPTION OF THE EMBODIMENTS

Now, the present invention will be described in greater detail by referring to the accompanying drawings that illustrate preferred embodiments of the invention. Throughout the drawings, same or similar components are denoted respectively by the same reference symbols. While a tera-hertz wave is used in the following description, an electromagnetic wave having a frequency other than frequency range of tera-hertz waves may alternatively be used depending on the frequency characteristics of the dielectric material of the transmission path and the configuration and the material of the components.

Figure 1:
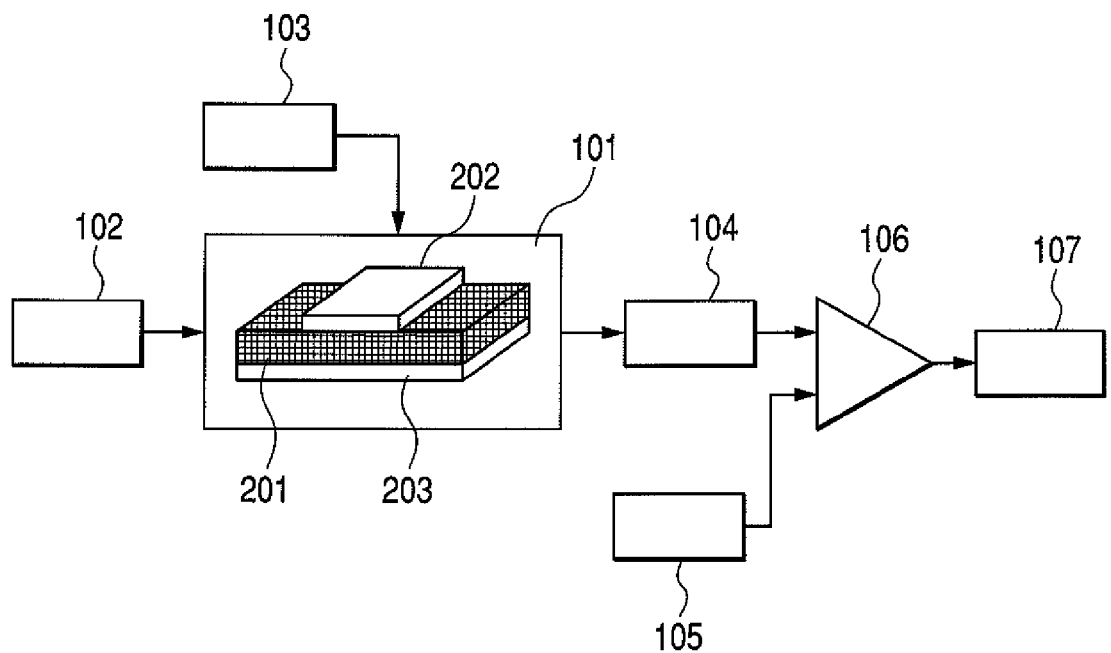
FIG. 1 is a schematic illustration of an embodiment of a specimen testing apparatus according to the invention that is used in an example, showing the configuration thereof.

FIG. 1 is a schematic illustration of an embodiment of a specimen testing apparatus according to the invention, showing the configuration thereof. As shown in FIG. 1, this embodiment of the specimen testing apparatus comprises a specimen testing element 101 adapted to operate for detection by means of a tera-hertz wave, an electromagnetic wave generating means 102 for controlling the tera-hertz wave to be used for detection and a specimen filling means 103 for filling the specimen testing element 101 with a specimen. The embodiment further comprises an electromagnetic wave detecting means 104 for detecting the tera-hertz wave output from the specimen testing element 101 and a database 105 storing information on physical properties of specimens. In FIG. 1, a comparing section 106 compares the output of the electromagnetic wave detecting means 104 and the information of the database 105 and a presenting section 107 presents the outcome of the comparison made by the comparing section 106.

Figure 2:
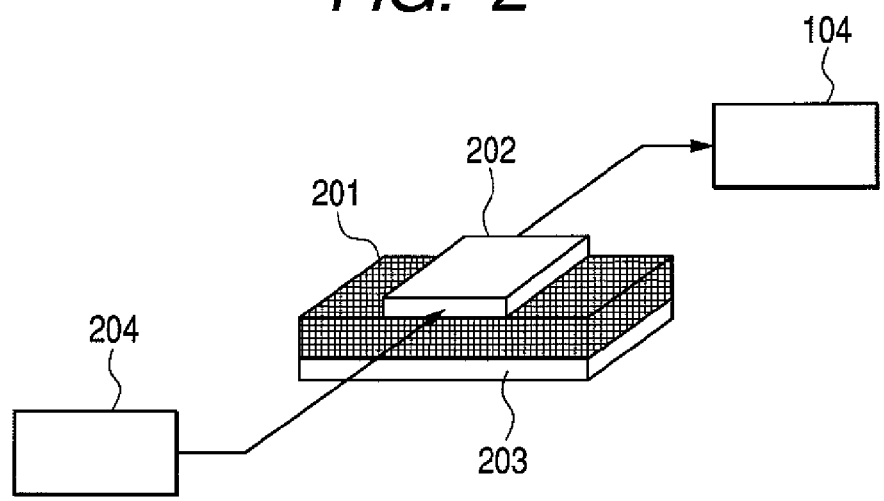
FIG. 2 is a schematic illustration of the configuration of the specimen testing element of FIG. 1.

FIG. 2 is a schematic illustration of the configuration of the specimen testing element 101 of FIG. 1. As shown in FIG. 2, the specimen testing element 101 in FIG. 1 comprises a specimen holding body 201 having voids (holding portions) with a modulated refractive index and a transmission path made of a conductor and a coupling means 204 is connected to the testing element. The specimen holding body 201 is formed by arranging a plurality of holding portions capable of holding a specimen substantially in a predetermined mode of regularity in part of the region in the transmission path where the propagating electromagnetic wave exists. However, the holding portions may not necessarily be voids with a modulated refractive index. For example, they may alternatively be so arranged that the refractive index is modulated as a result of filling the holding portions with the specimen.

Figure 5A:
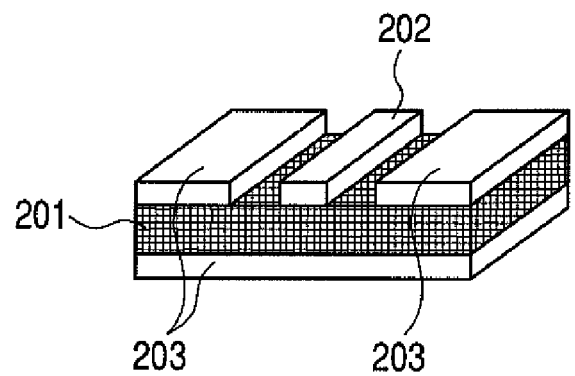
FIGS. 5A, 5B, 5C, 5D and 5E are schematic perspective views of the transmission path structure of a specimen testing element according to the present invention, illustrating several possible alternative configurations thereof.
Figure 5B:
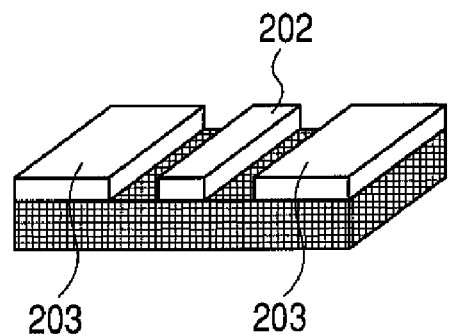
Figure 5C:
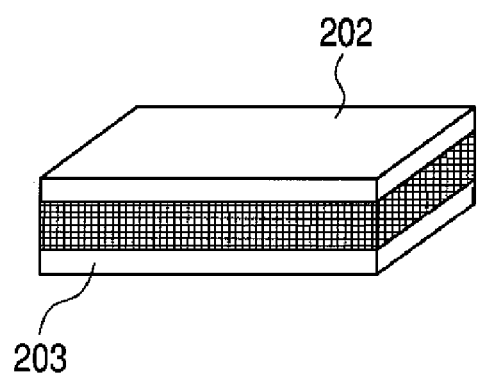
Figure 5D:
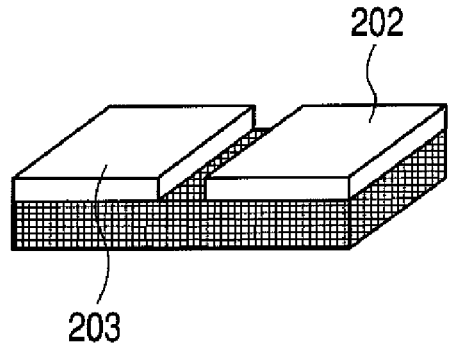
Figure 5E:
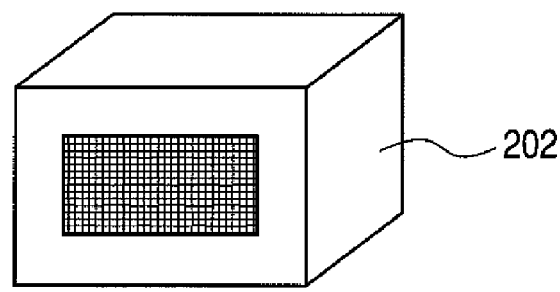

In this embodiment, the specimen testing element 101 will be described as a micro-strip line type testing element. Therefore, the testing element has a micro-strip line type structure where the specimen holding body 201 is sandwiched between a first conductor 202 and a second conductor 203 as shown in FIG. 2. However, the structure of the transmission path is not limited to that of a micro-strip line. For example, as shown in FIGS. 5A through 5E, the transmission path may alternatively have a coplanar waveguide structure having a ground (FIG. 5A), a coplanar waveguide structure (FIG. 5B), a parallel-plate waveguide structure (FIG. 5C), a strip line waveguide structure (FIG. 5D) or a tubular waveguide structure (FIG. 5E). In each of these structures, one or more than one conductor are made to adhere to the specimen holding body 201 and the structure shows a profile adapted to confine an electromagnetic wave therein so as to propagate the electromagnetic wave through it. When the transmission path has a tubular waveguide structure (FIG. 5E) or the like, the inside thereof except the specimen holding body 201 may be made hollow.

The specimen holding body 201 has a plurality of voids with a modulated refractive index for holding a specimen. However, the voids may be replaced by a substance that can be immersed with a specimen. The structure of the specimen holding body 201 may have a micro-structure that can easily adsorb a specimen. Additionally, the structure may be appropriately subjected to a surface treatment. For example, if the specimen is hydrophilic, the surface of the structure may be subjected to a surface treatment so that the voids may reliably be filled with the specimen. Alternatively, the specimen holding body 201 may be made of a material that is immersed with the specimen or reacts with the specimen to change the physical properties. In short, the specimen holding body 201 is so required that the modulated condition of the refractive index is changed by the specimen.

The voids of the specimen holding body 201 have a size of the order of the wavelength of the electromagnetic wave to be used for the test. With the specimen holding body 201 having a plurality of voids of such a size, it is possible to produce a specific phenomenon arising from a band gap such that it does not allow any electromagnetic wave of a specific frequency band to propagate. The voids may vary self-similarly relative to the electromagnetic wave to be used for the test. When the specimen holding body 201 has such voids, it is possible to produce a phenomenon such that a specific electromagnetic wave is localized in the specimen holding body 201. The voids may be arranged two-dimensionally or three-dimensionally so long as they are arranged in such a way that the physical properties (e.g., the dielectric constant) of the specimen holding body 201 will vary in a certain mode of regularity due to the voids. Then, it is possible to provide the transmission path with specific functional features such as wavelength selectivity and/or particular resonance characteristics when such a specimen holding body 201 is used as the substrate of the transmission path. Depending on the application, a structure that disturbs the regularity of modulation of a refractive index may be introduced by filling the voids with the material of the specimen holding body 201 or some other material or introducing additional voids. In short, it is only necessary that a plurality of holding portions capable of holding a specimen are arranged substantially in a predetermined mode of regularity.

In this embodiment, the transmission path of the structure of the testing element is provided with a coupling means 204 as shown in FIG. 2. The coupling means 204 couples a tera-hertz wave to the structure of the testing element and propagates the former. As described above, since the testing element of this embodiment has a micro-strip line type structure, the coupling means 204 operates to couple a tera-hertz wave to the micro-strip line type testing element comprising the specimen holding body 201, the first conductor 202 and the second conductor 203. The coupling means 204 of this embodiment may additionally have a functional feature of coupling the tera-hertz wave that is generated in the inside of the coupling means 204 to the micro-strip line type testing element in addition to the above-described functional feature of coupling the tera-hertz wave coming from the outside to the micro-strip line type testing element.

FIGS. 3A, 3B, 3C and 3D are schematic plan views of the coupling means 204 of the specimen testing element of FIG. 1 for coupling a tera-hertz wave to the testing element, illustrating several possible alternative configurations thereof. Since the specimen testing element 101 of this embodiment is a micro-strip line type testing element, the coupling means 204 is desirably of the micro-strip line type. However, the configuration of the coupling means 204 is not limited to that of the micro-strip line type and may be changed depending on the configuration of the testing element 101 that the embodiment comprises, which may vary as shown in FIGS. 5A through 5E. In other words, the configuration of the coupling means 204 is not limited to those illustrated in FIGS. 3A through 3D so long as the coupling means 204 is adapted to couple a tera-hertz wave to the testing element 101 and propagate the former.

Figure 3A:
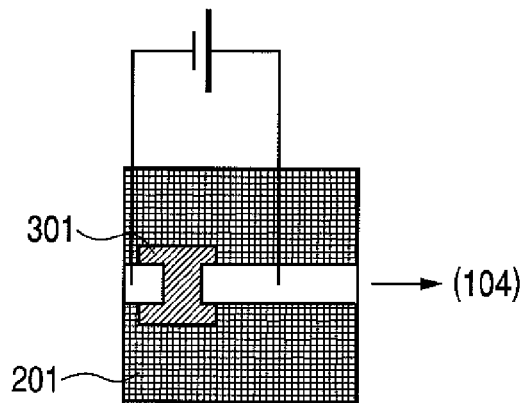
FIGS. 3A, 3B, 3C and 3D are schematic plan views of the coupling means of the specimen testing element of FIG. 1, illustrating several possible alternative configurations thereof.
Figure 3B:
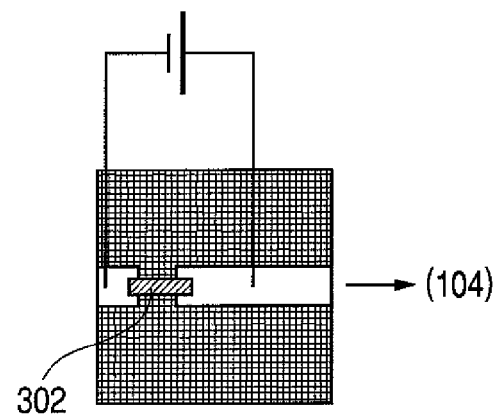
Figure 3C:
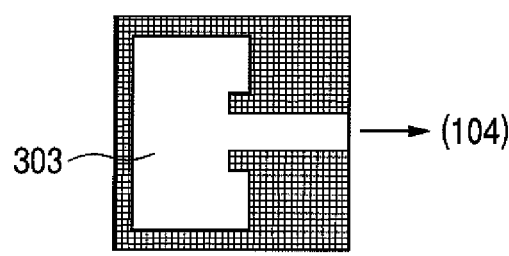
Figure 3D:
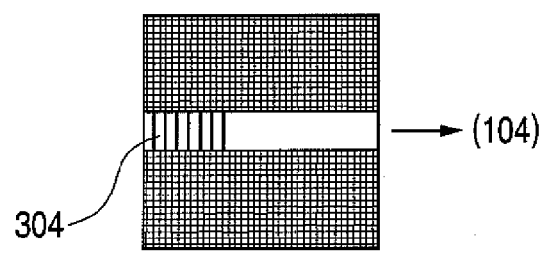

For example, when the coupling means 204 couples a tera-hertz wave coming from the outside to the testing element, an arrangement of using an antenna structure 303 as shown in FIG. 3C or an arrangement of using a grating structure 304 as shown in FIG. 3D may be suitable. The antenna structure 303 is only required to have a frequency characteristic adapted to detect the tera-hertz wave coming from the outside. Therefore, while FIG. 3C shows a resonance type patch antenna structure, the antenna structure is by no means limited thereto and any known antenna structure may alternatively be used. The grating structure 304 is obtained by preparing periodically arranged undulations on the conductor of the coupling means 204 as a function of the wavelength of the tera-hertz wave coming from the outside. Thus, it is possible to selectively couple a tera-hertz wave of a specific wavelength to the testing element 101 that is selected by the period of arrangement of undulations. The electromagnetic wave generating means 102 of FIG. 1 operates as source for generating a tera-hertz wave that is irradiated onto the specimen testing element 101. The electromagnetic wave generating means 102 may be formed as any known means adapted to generate tera-hertz waves.

When the coupling means 204 generates a tera-hertz wave in the inside thereof and couples it to the testing element, an arrangement of using an optical switch 301 as shown in FIG. 3A or an arrangement of using a gain material 302 as shown in FIG. 3B may possibly be employed. An optical switch 301 has a structure formed by arranging a slit in part of a conductor and a semiconductor showing a high carrier mobility and a short carrier life time (e.g., low temperature grown gallium arsenide: LT-GaAs) is made to adhere to the slit. An optical switch 301 operates to generate a tera-hertz wave when it is optically gated from the outside by means of a femtosecond-pulse laser beam under a condition of applying an electric field to the slit section of the conductor. Since the specimen testing element 101 is of the micro-strip line type, the generated tera-hertz wave is coupled to the testing element structure and propagates. When an optical switch 301 is used for the coupling means 204, the electromagnetic wave generating means 102 of FIG. 1 is made to comprise a means for applying an electric field to the slit section of the optical switch 301 and a means for irradiating a femtosecond-pulse laser beam from the outside (not shown).

When a gain material 302 is used for the coupling means 204 as shown in FIG. 3B, the gain material 302 is typically a semiconductor element such as a resonant tunneling diode (RTD) or a Gunn diode that is adapted to obtain an electromagnetic wave gain. As shown in FIG. 3B, the conductors of the testing element are provided with a slit and the gain material 302 is connected to the slit section. Alternatively, although not shown, the gain material 302 may be connected between the two conductors (the first conductor 202 and the second conductor 203 in FIG. 2) of the testing element. The gain material 302 is designed to obtain a gain in a desired frequency band of tera-hertz waves. Therefore, a tera-hertz wave is generated by applying an electric field between the opposite ends of the gain material 302. Since the specimen testing element 101 is of the micro-strip line type, the generated tera-hertz wave is coupled to the testing element structure and propagates. When a gain material 302 is used for the coupling means 204, the electromagnetic wave generating means 102 of FIG. 1 is made to comprise a means for applying an electric field to the gain material 302.

Figure 4:
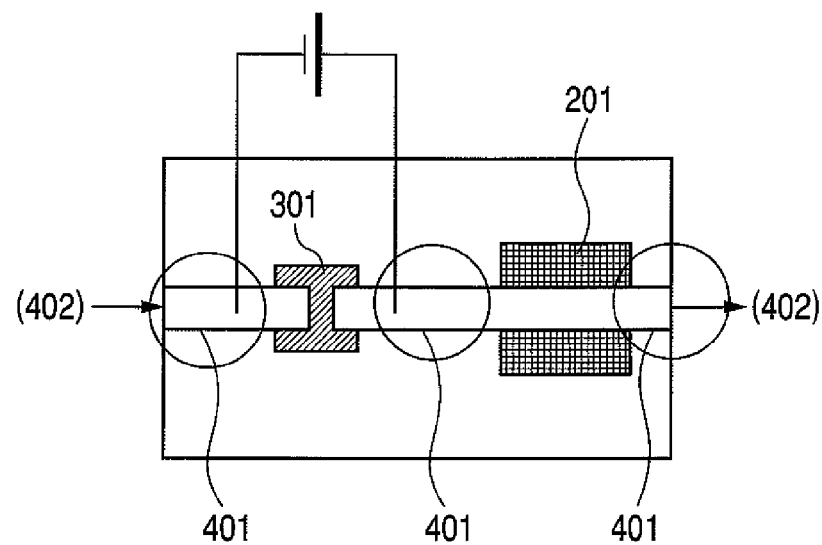
FIG. 4 is a schematic plan view of a specimen testing element according to the present invention, illustrating the configuration thereof.

Referring to FIGS. 3A through 3D, the coupling means 204 is formed on the specimen holding body 201 and integrated with the testing element structure of FIG. 2 to form the specimen testing element 101. However, the structure of the specimen testing element 101 is not necessarily limited thereto. For example, the coupling means 204 (where an optical switch 301 is used as an exemplar arrangement) and the testing element formed in the part of the specimen holding body 201 may be separated by means of relay transmission path (line) 401 as shown in FIG. 4. With such an arrangement, the process of preparing the specimen testing element 101 may be simplified because it is only necessary to form a specimen holding body 201 at a place where the specimen is to be tested. Additionally, since the specimen can be made to be found only in the testing part, the influence of the specimen on some other external circuit 402 (e.g., the electromagnetic wave generating means 102 for driving the coupling means 204 to operate) that may arise depending on the physical properties of the specimen can be alleviated to make it possible to conduct a test highly stably. Still additionally, such an arrangement provides an effect of raising the degree of freedom of laying out the element. Furthermore, it can reduce the cost of the testing element itself when the testing part is made replaceable.

Returning back to FIG. 1, now the embodiment of a specimen testing apparatus will be described below. As described above, the electromagnetic wave generating means 102 is an external circuit for controlling the coupling means 204 so as to couple a tera-hertz wave to the testing element 101 and propagate it. As pointed out above, the structure of the electromagnetic wave generating means 102 depends on the structure of the coupling means 204.

The specimen filling means 103 is only required to operate to fill the specimen to be tested in the voids of the specimen holding body 201 of the specimen testing element 101. For example, a mechanism adapted to be controlled typically by means of an actuator so as to drop the specimen from the tip of a probe and immerse the specimen into the specimen holding body 201 may be used in order to control the quantity of the specimen and/or the position to be filled with the specimen. An arrangement of injecting a predetermined quantity of the specimen like an inkjet system by means of an actuator may alternatively be used. Still alternatively, a mechanism for adding a substance that modifies the state of the specimen to the latter may be used.

The electromagnetic wave detecting means 104 operates to detect the tera-hertz wave propagating through the specimen testing element 101. The electromagnetic wave detecting means 104 may be adapted to operate with a known tera-hertz wave detecting technique. For example, an optical switch 301 as shown in FIG. 3A may be arranged in the transmission path of the specimen testing element 101 and gated by means of a femtosecond-pulse laser beam to sample the tera-hertz wave. Alternatively, the change in the polarization of light that is produced by the tera-hertz wave may be obtained by means of a substance having a nonlinear optical effect on tera-hertz waves. Still alternatively, the tera-hertz wave may be detected by means of a gain material 302 as in the case of other high frequency technologies. Still alternatively, the tera-hertz wave propagating through the specimen testing element 101 may be taken out to the outside once by means of an antenna structure 303 as shown in FIG. 3C or a grating structure 304 as shown in FIG. 3D and detected separately by means of any of the above-described techniques. It may be needless to say that detection techniques that can be used for detecting the tera-hertz wave are not limited to those described above, but an any technique that can achieve the objective of obtaining a tera-hertz wave may be used for the purpose of the present invention.

The database 105 is a storage memory for storing physical information on the specimen to be tested. The database 105 may store physical information on the specimen in advance or may be adapted to store the information obtained as a result of observing the specimen. Preferably, the database 105 stores physical information and other information on as many materials as possible.

The comparing section 106 transforms, if necessary, the tera-hertz wave detected by the electromagnetic wave detecting means 104 and performs a processing operation of comparing the obtained information on the tera-hertz wave and the information in the database 105. The comparing section 106 may perform all the operation of comparing the obtained information and the information in the database 105 by information processing or all or part thereof by means of one or more than one circuits.

The presenting section 107 operates to present the outcome of the comparison made by the comparing section 106 by using the physical information on the specimen to the outside.

A display apparatus may typically be used for presenting the outcome, although the present invention is by no means limited to the use of a display apparatus and any other mode of operation of presenting the outcome of the comparison may be used by the presenting section 107. For example, the outcome of the comparison may be notified to the operator by a change in the lighting state of one or more than one light emitting element. The presenting section 107 may appropriately be so arranged as to be removably fitted to the specimen testing apparatus.

Now, the operation of the specimen testing apparatus of this embodiment will be described below. The specimen testing element 101 has the specimen holding body 201 at least as part thereof. The specimen holding body 201 is adapted to operate with two materials having different physical properties (e.g., the material of the specimen holding body 201 and air). When different materials are arranged so as to modulate physical properties, the specimen holding body 201 explicitly shows wavelength selectivity and resonance characteristics relative to the electromagnetic wave propagating through it. Assume here that the specimen holding body 201 shows wavelength selectivity attributable to a band gap relative to the tera-hertz wave being used. As described above, the specimen holding body 201 is a substrate that operates to form a transmission path (which is of the micro-strip line type as pointed out above). The fact that the substrate operating to form a transmission path shows wavelength selectivity means that the propagation characteristics of the transmission path explicitly show wavelength selectivity.

A phenomenon as described below takes place when a specimen is filled in the voids of the specimen testing element 101 by the specimen filling means 103. The wavelength selectivity that has been defined so far by the relationship between the physical properties of the material of the specimen holding body 201 and those of air is redefined by the relationship between the physical properties of the material of the specimen holding body 201 and those of the specimen. The wavelength selectivity changes as a function of not only the presence or absence of the specimen in the voids but also the variety of the structure of the specimen which, for example, may be a single strand DNA or a double strand DNA if the specimen is a DNA. Thus, the frequency characteristics of the specimen testing element 101 change as the wavelength selectivity is positionally shifted. Information including physical information on the specimen is obtained by detecting such changes by means of the change in the propagation state of the tera-hertz wave.

When the above-described technique is used, it is desirable to know the propagation state of the tera-hertz wave in advance when the specimen does not exist yet. More specifically, the propagation state may be stored in advance as reference in the comparing section 106 and/or the database 105 when the specimen does not exist yet and information including physical information on the specimen may be obtained by means of the shift from the reference. However, the present invention is by no means limited to such a technique. For example, the propagation state of the tera-hertz wave may be observed immediately before a testing operation when the specimen does not exist yet and the obtained data may be stored in the comparing section 106 and/or the database 105 so as to be used as reference.

When the specimen to be tested is also anchored, the database 105 may not necessarily be required because it is possible to conduct a testing operation on the basis of the presence or absence of propagation of a tera-hertz wave and the change in the intensity of the tera-hertz wave that arises by a change in the wavelength selectivity (which may be determined by using a threshold value). When detecting the variety of the structure itself of the specimen, the structural difference can be detected by comparing the propagation state of a structure and that of another structure, using one of the structures as reference. Similarly, it is also possible to detect the change, if any, in the characteristics of the specimen by comparing the propagation state of an electromagnetic wave under a condition, which is used as reference, and that of the electromagnetic wave in a specimen that changes according to external stimuli (atmosphere, light, temperature, etc.). In this way, it is possible to analyze and identify a specimen according to physical information of the specimen like a bio sensor or a chemical sensor.

In this embodiment, a plurality of voids whose refractive index is modulated in the order of the wavelength of tera-hertz wave are provided and a specimen is held in the void sections so as to detect physical properties of the specimen by observing the change in the propagation state of the tera-hertz wave that is coupled to the specimen testing element. Therefore, it is possible to use not the tera-hertz wave that leaks out to the outside of the transmission path but the tera-hertz wave that is coupled to the specimen testing element. Thus, according to the present invention, it is possible to provide a specimen testing element that is hardly influenced by the external atmosphere, which may typically be represented by the moisture in the atmosphere. Additionally, since a tera-hertz wave that is coupled to the specimen testing element is employed, a specimen testing apparatus according to the present invention provides an advantage of an improved detection sensitivity because the tera-hertz wave that takes part in the detection can be enhanced in the specimen testing element of the specimen testing apparatus if compared with a testing element adapted to use a tera-hertz wave leaking out to the outside.

When the specimen is held by a structure where the refractive index is modulated in the order of the wavelength of tera-hertz wave, the mechanism for holding the specimen operates as resonator to make it possible to localize the tera-hertz wave to the area to be used for detection so that it is possible to improve the detection sensitivity. At the same time, since the detection sensitivity is improved, it is possible to detect a minor amount of a specimen by holding the specimen in a periodic structure of the order of the wavelength of the tera-hertz wave. Additionally, when the specimen can strongly absorb a tera-hertz wave, it is possible to reduce the amount of the specimen to be held in contact with the tera-hertz wave, while securing a region where the tera-hertz wave and the specimen interact with each other, because the specimen is partitioned by the structure for holding the specimen. Therefore, the present invention provides an advantage of easily and highly sensitively detecting a specimen if the specimen can strongly absorb a tera-hertz wave.

Now, the present invention will be described further by way of examples and by referring to the accompanying drawings.

EXAMPLE 1

Figure 6:
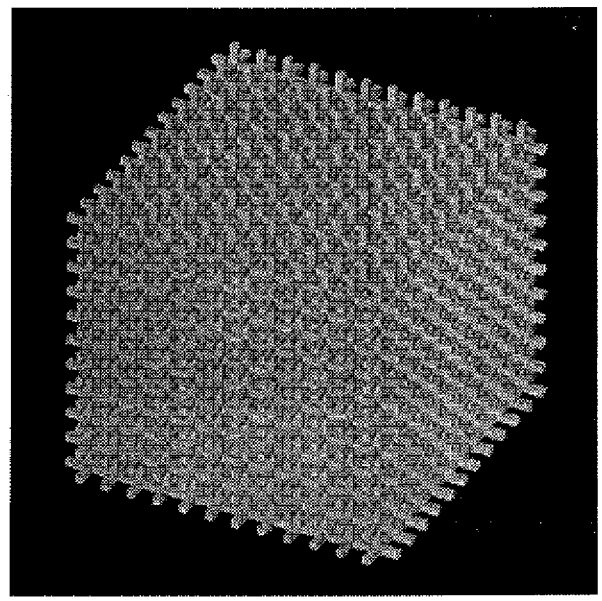
FIG. 6 is a schematic perspective view of the specimen holding body of Example 1.

In Example 1, a structure where voids are monotonously and periodically arranged in the material of a specimen holding body is used for the specimen holding body 201. A specimen holding body 201 having such a structure may be a simple cubic lattice type specimen holding body as shown in FIG. 6. While a simple cubic lattice type specimen holding body 201 is used in this example, the present invention is by no means limited to such a structure. As pointed out earlier, such a periodic structure is characterized by having a wavelength selectivity attributable to a photonic band gap.

The specimen holding body 201 is preferably made of a material showing characteristics that are remarkably different from the material characteristics of the void sections and transparent relative to tera-hertz waves. This is because, when the dielectric constant of the material is considered as a material characteristic, the wavelength selectivity that is attributable to a photonic band gap appears remarkably if the material characteristic is sufficiently large or small relative to that of the void sections. The material of the specimen holding body 201 is preferably transparent relative to tera-hertz waves for the reason as described below. When there exist a large number of carriers that can move freely relative to a tera-hertz wave in a material, the carriers fluctuate relative to the propagation of the tera-hertz wave. Then, noises may be produced and/or the signal intensity may become insufficient as the tera-hertz wave is dispersed. As a result, there arises a problem that the wavelength selectivity is not sufficient.

In this example, high resistance silicon (SI-Si, dielectric constant: 11.4, conductivity: 0.01 S/m) is used as the material of the specimen holding body 201. This material is known to be sufficiently transparent relative to tera-hertz waves. In this example, a simple cubic lattice is formed in high resistance silicon in such a way that it shows a lattice constant of 0.4 μm and each side of the voids is 0.11 μm long. Such a specimen holding body 201 can be prepared by means of a known MEMS (micro electro mechanical system). For example, periodic structure substrates of a cycle period for the height direction of the specimen holding body 201 are prepared by photolithography using a high resistance silicon substrate and the periodic structure substrates are bonded one on the other to get to desired cycle periods. In this example, the periodic structure substrates are prepared for ten cycle periods to form a simple cubic lattice. In other words, ten periodic structure substrates are laid one on the other to form a simple cubic lattice.

Figure 8:
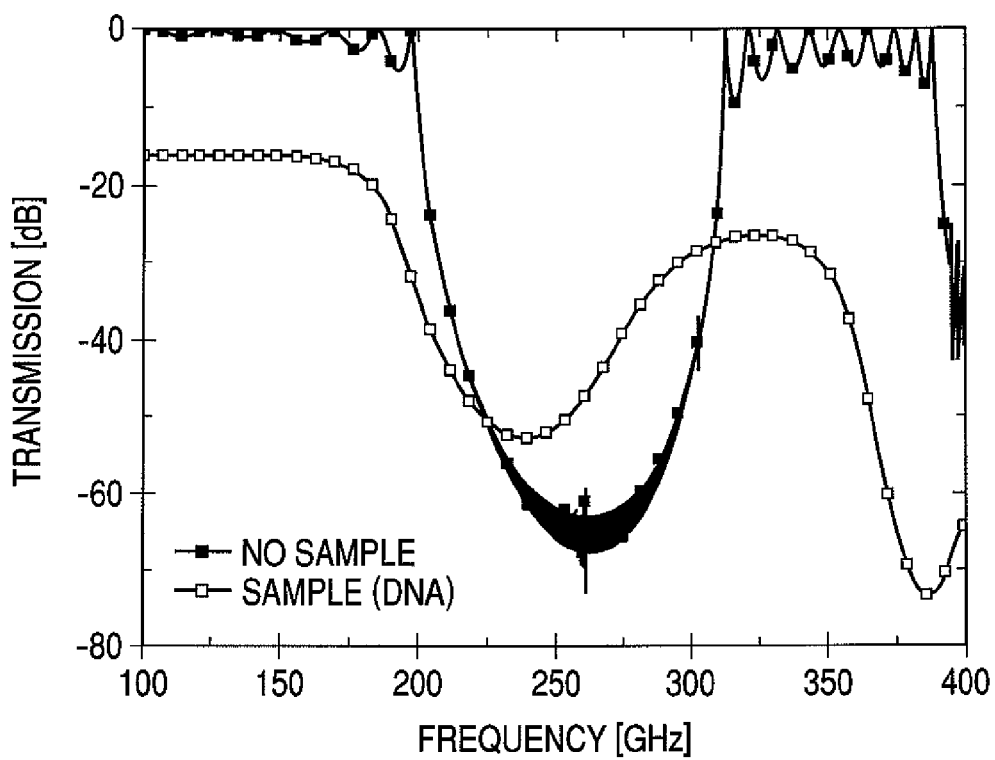
FIG. 8 is a graph illustrating the outcome of a computational operation conducted for the testing element of Example 1.

When a specimen exists in the void sections of the specimen holding body 201 prepared in this way, the wavelength selectivity of the specimen holding body 201 changes because the relationship of the material characteristics of the void sections with reference to those of the material of the specimen holding body 201 changes (between the material characteristics of air and those of a specimen in this example). FIG. 8 is a graph illustrating the outcome of a computational operation conducted for the propagation characteristic of a tera-hertz wave in the Γ-Z direction relative to the specimen holding body 201. The specimen is a DNA (dielectric constant: 4.0, dielectric tangent tan δ: 0.01). As seen from FIG. 8, a photonic band gap that is centered at 260 GHz exists when no specimen exists in the void sections. It will be seen from the graph of FIG. 8 that the photonic band gap is shifted to the lower frequency side by about 40 GHz and at the same time, the transmittance falls when a specimen is put into the void sections. Thus, it is possible to identify the material of the specimen from the frequency shift and the attenuation characteristic of the signal.

It is possible to detect not only the presence or absence of a specimen, as described above, but also the change, if any, in the structure and/or the characteristics of the specimen itself. While a simple cubic lattice is used in this example, a structure that disturbs a periodic structure such as a defect structure may be introduced into the periodic structure. In such a case, a region where electromagnetic waves are transmitted appears locally in the band gap and the local change in the transmittance of an electromagnetic wave may be used to observe the specimen.

In this example, a first conductor 202 and a second conductor 203 are made to adhere to the specimen holding body 201 as shown in FIG. 2 to form a micro-strip line type testing element. Additionally, an optical switch 301 of FIG. 3A is provided as the coupling means 204 in FIG. 2 to form the specimen testing element 101. The optical switch 301 is formed by selectively applying LT-GaAs onto the specimen holding body 201 and sandwiching the LT-GaAs between the specimen holding body 201 and the first conductor having a gap of the order of microns. As an electric field and a femto-second-pulse signal are applied to the optical switch 301 by the electromagnetic wave generating means 102, the tera-hertz wave is coupled to the specimen testing element 101 and propagates. Wavelength selectivity attributable to a photonic band gap appears in the specimen testing element 101. Thus, when a specimen is dropped in the specimen testing element 101 by the specimen filling means 103 to fill the void sections of the specimen holding body 201, it is possible to detect physical characteristics of the specimen by detecting the tera-hertz wave coupled to the testing element.

EXAMPLE 2

Figure 7:
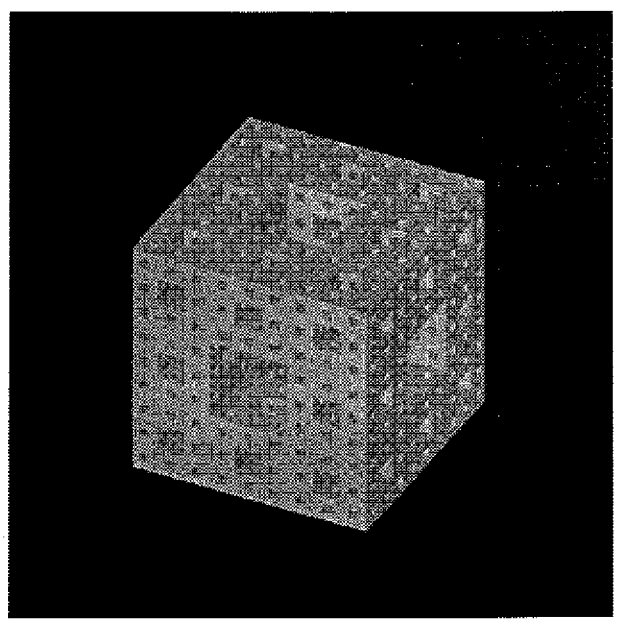
FIG. 7 is a schematic perspective view of the specimen holding body of Example 2.

In Example 2, a structure (fractal structure) where a plurality of voids are arranged in the material of the specimen holding body 201 is used so as to cause the modulation characteristics of the refractive index in the voids to self-similarly change. A Menger sponge type specimen holding body 201 as shown in FIG. 7 may be used as such a structure. While a Menger sponge type specimen holding body 201 is used in this example, the present invention is by no means limited to such a structure as pointed out above. Such a structure is referred to as photonic fractal structure and wavelength selectivity like that of a notch filter appears as a result of local existence of an electric field in the void parts that depends on the wavelength of the electromagnetic wave.

In this example again, the specimen holding body 201 is preferably made of a material showing characteristics that are remarkably different from the material characteristics of the void sections and transparent relative to tera-hertz waves as described above for Example 1.

As in Example 1, high resistance silicon (SI-Si, dielectric constant: 11.4, conductivity: 0.01 S/m) is used as the material of the specimen holding body 201. In this example, a cube having 135 μm long sides of such high resistance silicon is brought in and a cube having sides that are ⅓ of the sides of the first cube is removed from the body center and the surface center of the first cube (to be referred to as first stage operation) and the operation is repeated three times to obtain a structure (a photonic fractal structure of three stages). The specimen holding body 201 of this example can also be prepared by means of a known MEMS.

Figure 9:
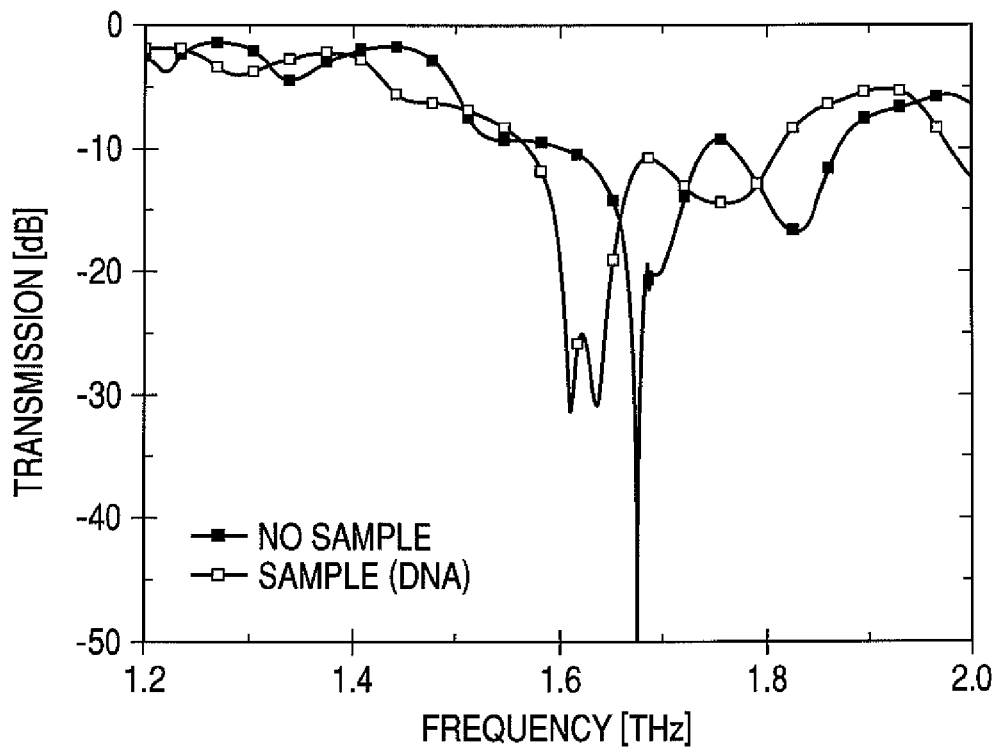
FIG. 9 is a graph illustrating the outcome of a computational operation conducted for the testing element of Example 2.
Figure 10:
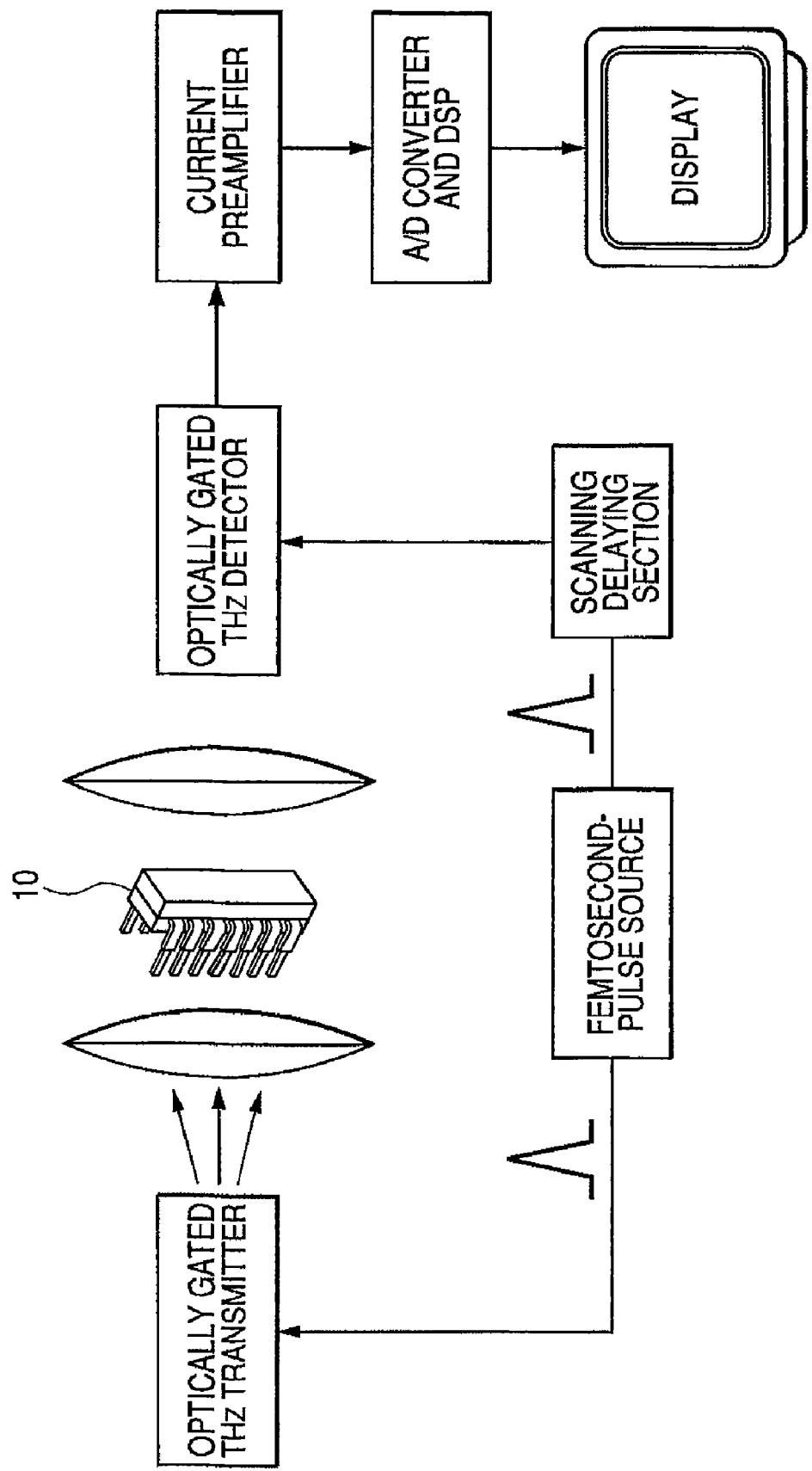
FIG. 10 is a schematic illustrating a known testing apparatus, showing the configuration thereof.
Figure 11:
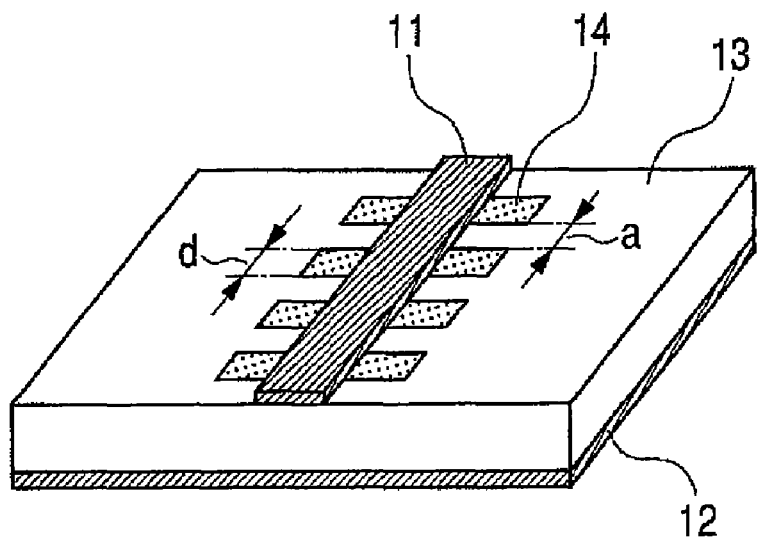
FIG. 11 is a schematic perspective view of an exemplar of a known transmission path for tera-hertz waves realized by using a substrate having a periodical structural part.
Figure 12:
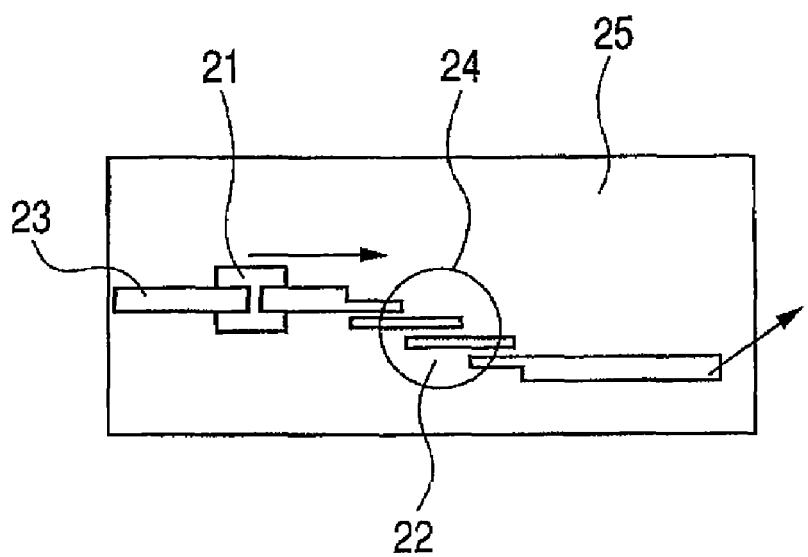
FIG. 12 is a schematic plan view of a known DNA sensor realized by using a transmission path.

When a specimen exists in the void sections of the specimen holding body 201 prepared in this way, the wavelength selectivity of the specimen holding body 201 changes because the relationship of the material characteristics of the void sections with reference to those of the material of the specimen holding body 201 changes (between the material characteristics of air and those of a specimen in this example again). FIG. 9 is a graph illustrating the outcome of a computational operation conducted for the propagation characteristic of a tera-hertz wave relative to the specimen holding body 201. The specimen is a DNA (dielectric constant: 4.0, dielectric tangent tan δ: 0.01). As seen from FIG. 9, the signal is selectively cut off at and near 1.68 THz when no specimen exists in the void sections. It will be seen from the graph of FIG. 9 that the cut off frequency is shifted to the lower frequency side by about 60 GHz and the propagation characteristic is broadened. Thus, it is possible to identify the material of the specimen from frequency shift and the change in the band width of the cut off frequency. It is possible to detect not only the presence or absence of a specimen, as described above, but also the change, if any, in the structure and/or the characteristics of the specimen itself.

In Example 2, a specimen testing element 101 is prepared by way of a process described above for Example 1. Wavelength selectivity that is specific to the fractal structure appears in the specimen testing element 101. Thus, when a specimen is dropped in the specimen testing element 101 by the specimen filling means 103 to fill the void sections of the specimen holding body 201, it is possible to detect physical characteristics of the specimen by detecting the tera-hertz wave coupled to the testing element.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-256545, filed Sep. 5, 2005, which is hereby incorporated by reference herein in its entirety.

What is claimed is:

1. A specimen testing element for obtaining information on a specimen by utilizing a change in the propagation state of an electromagnetic wave propagating through a transmission path due to an existence of the specimen, the electromagnetic wave having an appropriate band in a frequency range of 30 GHz to 30 THz, comprising:
   a plurality of holding portions, capable of holding a specimen, being arranged substantially in a predetermined mode of regularity to form a periodic structure having a wavelength selectivity attributable to a photonic band gap or a photonic fractal structure in part of a region in the transmission path where the propagating electromagnetic wave exists,
   wherein the transmission path has at least one conductor and a dielectric material and the plurality of holding portions are formed in the dielectric material, while the at least one conductor is formed to adhere to a surface of the dielectric material at least in order to confine the electromagnetic field to the sites where the plurality of holding portions exist.

2. The element according to claim 1, wherein the plurality of holding portions are formed by a silicon substrate of a cubic lattice type or of a Menger sponge type having many voids with a modulated refractive index in a predetermined space of the dielectric material.

3. The element according to claim 1, further comprising:
   coupling means for coupling an electromagnetic wave to the transmission path, said coupling means having an antenna structure or a grating structure to generate or detect an electromagnetic wave, to input an electromagnetic wave to the transmission path, or to output an electromagnetic wave from the transmission path.

4. A specimen testing apparatus comprising the specimen testing element according to claim 1, and further comprising:
   an ink jet system for jetting a specimen to the plurality of holding portions;
   electromagnetic wave generating means for propagating an electromagnetic wave through the transmission path; and
   electromagnetic wave detecting means for detecting an electromagnetic wave propagating through the transmission path.

5. The apparatus according to claim 4, further comprising:
   a database for storing information on specimens;
   a comparing section for collating the information of the database and electromagnetic wave information detected by the electromagnetic wave detecting means to obtain information on the specimen; and
   a presenting section for presenting the obtained information, wherein
   said presenting section includes a display apparatus for displaying an outcome of a comparison made by said comparing section.

6. The apparatus according to claim 4, further comprising:
   a database for storing information on specimens;
   a comparing section for collecting the information of the database and electromagnetic wave information detected by the electromagnetic wave detecting means to obtain information on the specimen; and
   a presenting section for presenting the obtained information, wherein
   said presenting section includes a light emitting element for notifying an outcome of a comparison made by said comparing section, by a change in a lighting state of the light emitting element.

7. An element, comprising:
   a transmission path for allowing a terahertz wave to propagate through the transmission path,
   the transmission path having a dielectric material and a conductor adhering to the dielectric material,
   said dielectric material including a holding portion for holding a specimen,
   said holding portion being arranged so that a specimen held by said holding portion can interact with a terahertz wave propagating through the transmission path,
   wherein said holding portion forms a periodic structure having a wavelength selectivity attributable to a photonic band gap or a photonic fractal structure to show a physical property which is changeable depending on the specimen held by said holding portion.

8. The element according to claim 7, wherein said holding portion comprises a silicon substrate of a cubic lattice type or of a Menger sponge type having a plurality of voids with a modulated refractive index or having a structure showing a modulated refractive index when said holding portion holds a specimen.

9. A specimen testing apparatus for obtaining information on a specimen comprising:
   the element according to claim 7, and
   jetting means for jetting a specimen to said holding portion, wherein said specimen detecting apparatus detects a change in a propagation state of a terahertz wave propagating through the transmission path by utilizing a change in wavelength selectivity caused when said jetting means jets a specimen to said holding portion.

10. The apparatus according to claim 9, further comprising:
   electromagnetic wave detecting means for detecting an electromagnetic wave propagating through the transmission path;
   a database for storing information on specimens;
   a comparing section for collating the information of the database and an electromagnetic wave detected by said electromagnetic wave detecting means;
   an obtaining section for obtaining a frequency shift and a change in attenuation characteristic or frequency band width of the electromagnetic wave detected by said electromagnetic wave detecting means using an outcome from said comparing section; and a specimen material identifying section for identifying the material of the specimen using an outcome from said obtaining section.

11. The element according to claim 7, wherein the terahertz wave has an appropriate band in the frequency range of 30 GHz to 30 THz.

12. The element according to claim 11, further comprising:
a gain material or an optical switch for generating the terahertz wave provided between a conductor of the transmission path and another conductor.

* * * * *